US00PP30287P3

(12) United States Plant Patent
Koekkoek

(10) Patent No.: US PP30,287 P3
(45) Date of Patent: Mar. 12, 2019

(54) CARNATION PLANT NAMED 'HILBECHGRE'

(50) Latin Name: *Dianthus caryophyllus*
Varietal Denomination: Hilbechgre

(71) Applicant: Arthur N. J. Koekkoek, Alkmaar (NL)

(72) Inventor: Arthur N. J. Koekkoek, Alkmaar (NL)

(73) Assignee: Hilverda Kooij B.V., De Kwakel (NL)

( * ) Notice: Subject to any disclaimer, the term of this patent is extended or adjusted under 35 U.S.C. 154(b) by 0 days.

(21) Appl. No.: 15/732,360

(22) Filed: Oct. 30, 2017

(65) Prior Publication Data

US 2018/0124977 P1 May 3, 2018

Related U.S. Application Data

(60) Provisional application No. 62/496,884, filed on Oct. 31, 2016.

(51) Int. Cl.
*A01H 5/02* (2018.01)
*A01H 6/30* (2018.01)

(52) U.S. Cl.
USPC ..... Plt./272
CPC ..... *A01H 5/02* (2013.01); *A01H 6/305* (2018.05)

(58) Field of Classification Search
USPC ..... Plt./272
See application file for complete search history.

*Primary Examiner* — Susan McCormick Ewoldt
(74) *Attorney, Agent, or Firm* — C. A. Whealy

(57) ABSTRACT

A new and distinct cultivar of Carnation plant named 'Hilbechgre', characterized by its compact, uniformly mounding and upright to broadly spreading plant habit; relatively small leaves; freely flowering habit; light yellow-colored double flowers with red purple-colored margins and apices; and good container and garden performance.

1 Drawing Sheet

Botanical designation: *Dianthus caryophyllus*.
Cultivar denomination: 'HILBECHGRE'.

BACKGROUND OF THE INVENTION

The present invention relates to a new and distinct cultivar of Carnation plant, botanically known as *Dianthus caryophyllus*, grown commercially as a container plant, previously known by the name 'Hilbchgrace' and hereinafter referred to by the name 'Hilbechgre'.

The new Carnation plant is a product of a planned breeding program conducted by the Inventor in De Kwakel, The Netherlands. The objective of the breeding program is to create new container Carnation plants with numerous attractive flowers.

The new Carnation plant originated from a cross-pollination made by the Inventor in De Kwakel, The Netherlands in April, 2012 of a proprietary selection of *Dianthus caryophyllus* identified as code number Fouta7626302, not patented, as the female, or seed, parent with a proprietary selection of *Dianthus caryophyllus* identified as code number A96166-10, not patented, as the male, or pollen, parent. The new Carnation plant was discovered and selected by the Inventor as a single flowering plant from within the progeny of the stated cross-pollination in a controlled greenhouse environment in De Kwakel, The Netherlands in September, 2012.

Asexual reproduction of the new Carnation plant by terminal vegetative cuttings propagated in a controlled greenhouse environment in De Kwakel, The Netherlands since January, 2014 has shown that the unique features of this new Carnation plant are stable and reproduced true to type in successive generations of asexual reproduction.

SUMMARY OF THE INVENTION

Plants of the new Carnation have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilbechgre'. These characteristics in combination distinguish 'Hilbechgre' as a new and distinct Carnation plant:

1. Compact, uniformly mounding and upright to broadly spreading plant habit.
2. Relatively small leaves.
3. Freely flowering habit.
4. Light yellow-colored double flowers with red purple-colored margins and apices.
5. Good container and garden performance.

Plants of the new Carnation differ primarily from plants of the female parent selection in the following characteristics:

1. Plants of the new Carnation are more compact than plants of the female parent selection.
2. Plants of the new Carnation and the female parent selection differ in flower color as plants of the female parent selection have pink-colored flowers.

Plants of the new Carnation differ primarily from plants of the male parent selection in the following characteristics:

1. Plants of the new Carnation have smaller flowers than plants of the male parent selection.
2. Flowers of plants of the new Carnation are more fully double than flowers of plants of the male parent selection.
3. Plants of the new Carnation and the male parent selection differ in flower color as plants of the male parent selection have white-colored flowers.

Plants of the new Carnation also can be compared to plants of *Dianthus Caryophyllus* 'Hilbechbon', not patented. In side-by-side comparisons, plants of the new Carnation differ primarily from plants of 'Hilbechbon' in flower color as plants of 'Hilbechbon' have dark yellow orange-colored flowers with pink-colored margins and apices.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant.

The photograph comprises a side perspective view of a typical flowering plant of 'Hilbechgre' grown in a container.

DETAILED BOTANICAL DESCRIPTION

Plants used in the aforementioned photograph and following observations and measurements were grown during the summer in 10.5-cm containers in a glass-covered greenhouse in De Kwakel, The Netherlands and under cultural practices typical of commercial container Carnation production. During the production of the plants, day temperatures ranged from 16° C. to 23° C. and night temperatures ranged from 13° C. to 18° C. Plants used for the photograph and description were 13 weeks from planting and were pinched one time at the time of planting. In the following description, color references are made to The Royal Horticultural Society Colour Chart, 2015 Edition, except where general terms of ordinary dictionary significance are used.

Botanical classification: *Dianthus caryophyllus* 'Hilbechgre'.

Parentage:

*Female, or seed, parent.*—Proprietary selection of *Dianthus caryophyllus* identified as code number Fouta7626302, not patented.

*Male, or pollen, parent.*—Proprietary selection of *Dianthus caryophyllus* identified as code number A96166-10, not patented.

Propagation:

*Type.*—By terminal vegetative cuttings.

*Time to initiate roots, summer.*—About six days at temperatures ranging from 20° C. to 25° C.

*Time to initiate roots, winter.*—About eight days at temperatures about 18° C.

*Time to produce a rooted young plant, summer.*—About three weeks at temperatures ranging from 20° C. to 25° C.

*Time to produce a rooted young plant, winter.*—About five weeks at temperatures about 18° C.

*Root description.*—Medium in thickness, fibrous; whitish in color.

*Rooting habit.*—Moderate branching; medium density.

Plant description:

*Plant and growth habit.*—Herbaceous perennial, typically grown as a container plant; compact, uniformly mounding, upright to broadly spreading plant habit; moderately vigorous growth habit.

*Plant height, soil level to top of foliar plane.*—About 15.4 cm.

*Plant height, soil level to top of floral plane.*—About 16.9 cm.

*Plant diameter or spread.*—About 18.3 cm.

*Lateral branches.*—Branching habit: Freely branching habit with about six main (basal) stems; each main stem with about five lateral branches; pinching enhances lateral branch development. Length: About 10.2 cm. Diameter: About 3.5 mm. Internode length: About 1.3 cm. Strength: Strong. Aspect: Upright to about 30° from vertical. Texture and luster: Smooth, glabrous, waxy cuticle; matte. Color, developing: Close to 145A to 145B; at internodes, close to 145B. Color, developed: Close to 144B; thin waxy cuticle, close to 190B.

Leaf description:

*Arrangement.*—Opposite, simple; sessile.

*Length.*—About 7.8 cm.

*Width.*—About 9 mm.

*Shape.*—Narrowly lanceolate; moderately to strongly curled.

*Apex.*—Acute.

*Base.*—Attenuate; decurrent.

*Margin.*—Entire.

*Texture and luster, upper and lower surfaces.*—Smooth, glabrous, waxy cuticle; slightly glossy.

*Venation pattern.*—Parallel.

*Color.*—Developing leaves, upper and lower surfaces: Close to 138A. Fully expanded leaves, upper surface: Close to NN137A; venation, close to NN137A; thin waxy cuticle, close to 189A. Fully expanded leaves, lower surface: Close to NN137A to NN137B; venation, close to 143A; thin waxy cuticle, close to 189A.

Flower description:

*Flower form and flowering habit.*—Double type flowers arranged singly or in pairs; freely flowering habit with about 36 flowers per plant at one time; flowers face mostly upright to slightly outwardly.

*Natural flowering season.*—Flowering is continuous from the spring to late summer in The Netherlands; plants begin flowering about 13 weeks after planting.

*Postproduction longevity.*—Flowers last about ten days on the plant; flowers not persistent.

*Fragrance.*—Faintly to moderately fragrant; clove-like, sweet and pleasant.

*Flower buds.*—Length: About 2.8 cm. Diameter: About 1.1 cm. Shape: Narrowly obovate. Texture and luster: Smooth, glabrous; matte. Color: Close to 143B to 143C; towards the base, close to 144B to 144C; petal apices, close to 2D and 71A.

*Flower diameter.*—About 4.9 cm.

*Flower depth.*—About 4.3 cm.

*Petals.*—Quantity and arrangement: About five petals arranged in a single whorl. Length: About 4 cm. Width: About 2.5 cm. Shape: Spatulate. Apex: Irregularly dentate and praemorse. Base: Narrowly cuneate. Margin: Distally, irregularly dentate; proximally, entire; undulate. Texture and luster, upper surface: Smooth, glabrous; velvety; matte. Texture and luster, lower surface: Smooth, glabrous; slightly velvety; matte. Color: When opening, upper surface: Close to 1D; at the margins and apex, close to 71B to 71C; at the base, close to 150D. When opening, lower surface: Lighter than 1D; at the margins and apex, close to 72B; at the base, close to 150D. Fully opened, upper surface: Close to 1D; at the margins and apex, close to 71C; at the base, close to 150D; venation, similar to lamina colors; colors do not change with development. Fully opened, lower surface: Lighter than 1D; at the margins and apex, close to 72B; at the base, close to 150D; venation, similar to lamina colors; colors do not change with development.

*Petaloids.*—Quantity and arrangement: About 35 petaloids arranged in about seven whorls. Length: About 2.5 cm to 3.9 cm. Width: About 0.7 cm to 2.4 cm. Shape: Spatulate. Apex: Irregularly dentate and praemorse. Base: Narrowly cuneate. Margin: Distally, irregularly dentate; proximally, entire; undulate. Texture and luster, upper and lower surfaces: Smooth, glabrous; slightly velvety; matte. Color: When opening, upper surface: Close to 1D; at the margins and apex, close to 71B to 71C; at the base, close to 150D. When opening, lower surface: Lighter than 1D; at the margins and apex, close to 72B; at the base, close to 150D. Fully opened, upper surface: Close to 1D; at the margins and apex, close to 71C; at the base, close to 150D; venation, similar to lamina colors; colors do not change with development. Fully opened, lower surface: Lighter than 1D; at the margins and apex, close to 72B; at the base, close to 150D; venation, similar to lamina colors; colors do not change with development.

*Sepals.*—Quantity and arrangement: Five sepals arranged in a single whorl; proximal 80% portion of the sepals are fused into a campanulate-shaped calyx. Calyx length: About 2.5 cm. Calyx diameter: About 2 cm. Sepal length: About 2.5 cm. Sepal width, at base of "free" portion: About 8 mm. Shape: Obovate. Apex: Acute. Margin: Entire. Texture and luster, upper and lower surfaces: Smooth, glabrous; slightly glossy. Color: When opening, upper surface: Close to 192A; at the apex and base, close to 145A. When opening, lower surface: Close to 143B to 143C; towards the base, close to 144B to 144C. Fully opened, upper surface: Close to 192A; at the apex and base, close to 145A. Fully opened, lower surface: Close to 143A to 143B; towards the base, close to 144B to 144C.

*Peduncles.*—Length: About 7 mm. Diameter: About 2 mm. Strength: Moderately strong. Aspect: About 35° from the stem axis. Texture and luster: Smooth, glabrous, waxy; matte. Color: Close to NN137D; thin waxy layer, close to 190B.

*Reproductive organs.*—Stamens: Quantity: About 35 stamens per flower; significantly deformed. Filament length: About 0.6 cm to 2.8 cm. Filament color: Close to 155B and 155C. Anther size: About 2 mm by 0.75 mm. Anther shape: Irregularly oblong, deformed. Anther color: Close to 160D. Pollen amount: Scarce. Pollen color: Close to 160B. Pistils: Quantity: About three per flower. Pistil length: About 3.2 cm. Stigma diameter: About 1 mm. Stigma shape: Pointed, curved. Stigma color: Close to 150D. Style length: About 3 cm. Style color: Close to 155C. Ovary color: Close to N144A. Fruits and seeds: Fruit and seed development have not been observed on plants of the new Carnation to date.

Disease & pest resistance: Plants of the new Carnation have not been observed to be resistant to pathogens and pests common to Carnation plants to date.

Garden performance: Plants of the new Carnation have been observed to tolerate rain, wind, high temperatures about 35° C. and to be suitable for USDA Hardiness Zones 5 to 9.

It is claimed:

1. A new and distinct Carnation plant named 'Hilbechgre' as illustrated and described.

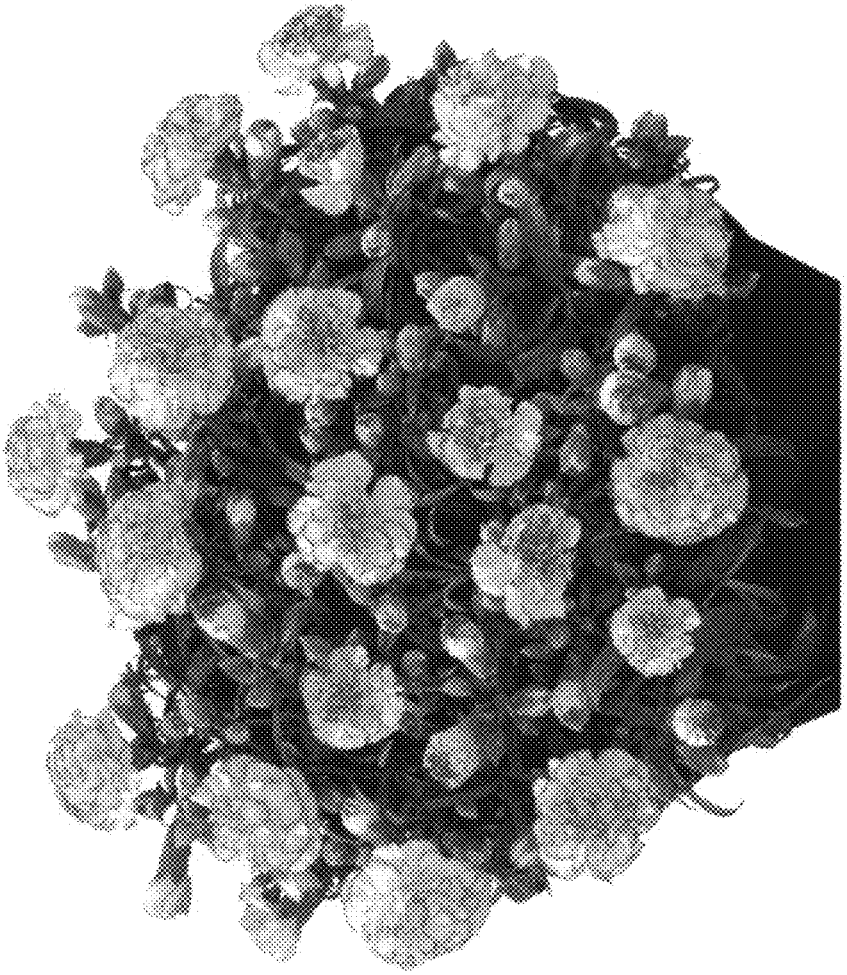

* * * * *